United States Patent
Eriksson et al.

(10) Patent No.: US 8,626,313 B2
(45) Date of Patent: Jan. 7, 2014

(54) PIEZOELECTRIC SENSOR, A METHOD FOR MANUFACTURING A PIEZOELECTRIC SENSOR AND A MEDICAL IMPLANTABLE LEAD COMPRISING SUCH A PIEZOELECTRIC SENSOR

(75) Inventors: Tom Eriksson, Sandviken (SE); Kenth Nilsson, Åkersberga (SE); Sven-Erik Hedberg, Kungsängen (SE)

(73) Assignee: St. Jude Medical, AB, Jarfalla (SE)

( * ) Notice: Subject to any disclaimer, the term of this patent is extended or adjusted under 35 U.S.C. 154(b) by 1169 days.

(21) Appl. No.: 12/298,218

(22) PCT Filed: Apr. 25, 2006

(86) PCT No.: PCT/SE2006/000479
§ 371 (c)(1),
(2), (4) Date: Jun. 25, 2009

(87) PCT Pub. No.: WO2007/123444
PCT Pub. Date: Nov. 1, 2007

(65) Prior Publication Data
US 2010/0010600 A1    Jan. 14, 2010

(51) Int. Cl.
*A61N 1/00* (2006.01)
*A61B 5/00* (2006.01)
*G01L 7/00* (2006.01)

(52) U.S. Cl.
USPC .............................. 607/116; 600/561; 73/700

(58) Field of Classification Search
USPC .............. 607/116; 600/561; 73/727, 730, 700
See application file for complete search history.

(56) References Cited

U.S. PATENT DOCUMENTS

| | | |
|---|---|---|
| 4,509,947 A | 4/1985 | Lattin |
| 4,697,595 A | 10/1987 | Breyer et al. |
| 4,802,481 A * | 2/1989 | Schroeppel ..................... 607/24 |
| 5,893,848 A * | 4/1999 | Negus et al. ..................... 606/41 |
| 6,069,845 A | 5/2000 | Ambs |
| 6,198,207 B1 | 3/2001 | Lally et al. |
| 6,547,788 B1 * | 4/2003 | Maguire et al. ................. 606/41 |
| 6,571,130 B1 | 5/2003 | Ljungström et al. |
| 6,587,709 B2 * | 7/2003 | Solf et al. ....................... 600/424 |
| 6,886,411 B2 * | 5/2005 | Kjellman et al. ............... 73/756 |
| 2010/0010600 A1 * | 1/2010 | Eriksson et al. .............. 607/116 |

FOREIGN PATENT DOCUMENTS

| | | |
|---|---|---|
| WO | WO 02/34130 | 5/2002 |
| WO | WO 2004/071684 | 8/2004 |

* cited by examiner

*Primary Examiner* — Mark W Bockelman

(57) ABSTRACT

In a piezoelectric sensor, a method for the manufacture thereof, and an implantable lead embodying such a piezoelectric sensor, a layer of piezoelectric material, having aligned, polarized dipoles, is applied to a tubular supporting substrate, the layer of piezoelectric material having at least one electrode at an outer surface thereof and at least one electrode at an inner surface thereof. The piezoelectric material is applied on the inner circumference of the tubular supporting substrate.

5 Claims, 2 Drawing Sheets

PIEZOELECTRIC SENSOR, A METHOD FOR MANUFACTURING A PIEZOELECTRIC SENSOR AND A MEDICAL IMPLANTABLE LEAD COMPRISING SUCH A PIEZOELECTRIC SENSOR

BACKGROUND OF THE INVENTION

1. Field of the Invention

The invention relates to a piezoelectric sensor having a layer of a piezoelectric material being applied to a supporting substrate.

The invention also relates to a method for manufacturing of such a piezoelectric sensor.

The invention also relates to a medical implantable lead comprising such a piezoelectric sensor.

2. Description of the Prior Art

Piezoelectric sensors of the above type are commonly used to detect and measure physical characteristics, such as fluid pressure, stress in mechanical structures and the like. Briefly, piezoelectric sensors transform deformations into electrical signals or pulses. Accordingly, they have a wide applicability and are frequently used in industrial and electronic applications.

A piezoelectric sensor of the above kind, may also be used in many different applications for monitoring various functions and organs inside a human or animal body. As such it may be used to monitor e.g. pressures inside tissue or body fluids. Hence, it can be used in for example a medical implantable lead connected to a pace maker to monitor blood pressure and/or heart rate inside a heart.

U.S. Pat. No. 6,571,130 discloses a medical implantable lead comprising a piezoelectric sensor, which in one embodiment is formed in a distal and surface of the lead and in another embodiment is formed as a ring or envelope surface of the lead.

Also, WO 02/34130 disclosed piezoelectric sensors for medical implantable leads, which are formed as tubes having the piezoelectric material applied on the outside of the supporting substrate or, on one embodiment, having the piezoelectric material formed as a self-supporting structure. On the outside, only a thin electrode layer is covering the outer surface of the piezoelectric sensor.

However, in many cases it is disadvantageous to have the piezoelectric material in direct contact with tissue and/or body fluids, e.g. blood, since then the piezoelectric material should preferably be made of a biocompatible and non-toxic material, which might exclude the use of certain materials that could have better characteristics in certain aspects, either electrically and/or mechanically.

Also the contacting of cables or coils to the electrodes can be problematic when in contact with body tissue or fluids since the connections, which normally are soldered or welded, will be more exposed.

SUMMARY OF THE INVENTION

It is an object of the invention to provide an improved piezoelectric sensor. More precisely it is an object of the invention to provide a piezoelectric sensor in which the piezoelectric material and electric connections will be more shielded in relation to the environment.

The invention also relates to a method for manufacturing of a piezoelectric sensor and a medical implantable lead comprising such a piezoelectric sensor, having essentially the same object as above.

The invention is based on the insight that the above objects may be achieved by arranging the piezoelectric material on the inner circumference of a tubular supporting substrate. In this way the piezoelectric material and the electrical connections will be better protected against environmental influence and it is also possible to easily shield the piezoelectric material completely from the environment.

Within this general idea, the invention can be realized in many different ways. Although preferred, it is not necessary that the piezoelectric sensor is cylindrical and formed with a circular cross section. On the contrary it is possible to have other cross sectional shapes as for example triangular, square, other polygonal shapes, oval or other arbitrary, regular or irregular shapes. The piezoelectric sensor could also be conical or truncated conical in longitudinal section. Accordingly, the term "tubular" as used herein, is to be interpreted in an extensive way.

Furthermore, the shielding against the environment of the piezoelectric sensor can be accomplished in many different ways. If, for example, the piezoelectric sensor is formed with a through bore, the sensor can be built into the structure of an object, e.g. a medical implantable lead in which it is going to be used, such that the piezoelectric material will be fluid tight shielded against environmental fluids, gases as well as liquids. Alternatively, the inner cavity of the sensor, in which the piezoelectric layer is positioned, can be fluid tight sealed in itself. Still another alternative is that the sensor is formed with an inner cavity, which is sealed but the sensor is provided with a through bore for allowing lead-through of for example electrical leads, torque transmitting wires, coils or the like. One advantage with having a fluid tight sealing of the inner cavity, in which the piezoelectric material is positioned, is that the sensitivity of the sensor will be increased. This is due to the fact that when the piezoelectric layer is in direct contact with fluids, the sensor is reacting on the direct fluid pressure on the piezoelectric material, whereas when sealed off inside a cavity, the piezoelectric layer will react to stresses in the supporting substrate due to deformations when the pressure outside the sensor varies.

In a preferred embodiment, the supporting substrate also serves as the outer electrode for the piezoelectric sensor. In this way, the electrode can preferably be exposed to the environment, in e.g. a medical implantable lead, and used for the additional purpose of transmitting or receiving electrical signals to and from the environment, for example pacing signals to a heart in the case of a pacemaker lead. For this reason the supporting substrate can suitably be metallic, but it is also conceivable to use any other suitable, electrically conducting material, such as electrically conducting ceramics or plastics. However, it is within the scope of the invention, as is disclosed in a hereinafter described embodiment, that the supporting substrate can be electrically insulating, in which case a separate electrode is arranged between the piezoelectric material and the supporting substrate.

Usually, the piezoelectric sensor comprises only one unitary piezoelectric layer, in which case only two electrodes, one on each side of the piezoelectric layer, and two connection leads is required. However, it is also possible to provide the sensor with a piezoelectric layer, which is separated into two or more different piezoelectric areas, each having a separate connection lead, which either can be operated separately or be connected in a suitably way to be operated in cooperation.

DESCRIPTION OF THE PREFERRED EMBODIMENTS

Figure 1:
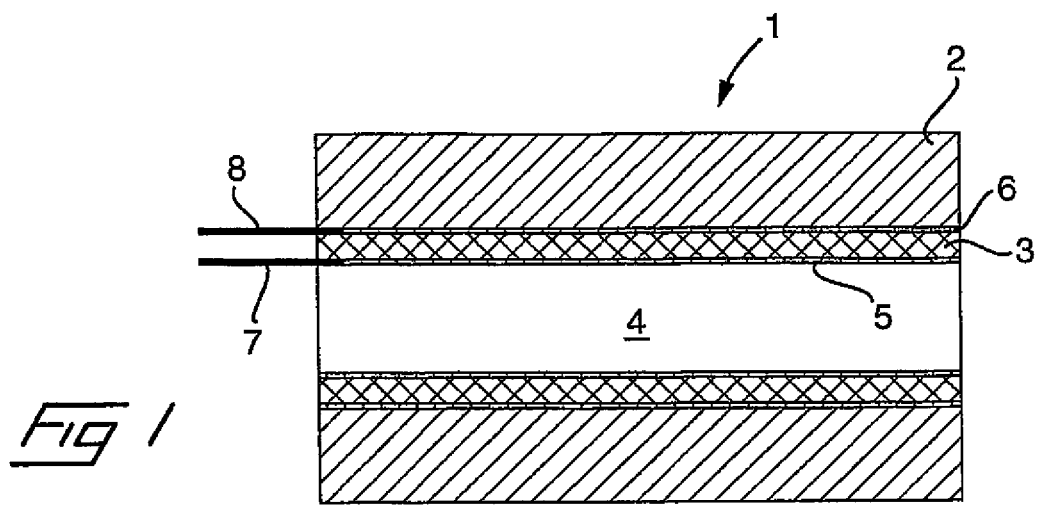
FIG. 1 is a longitudinal section through a piezoelectric sensor according to a first embodiment of the invention.
Figure 2:
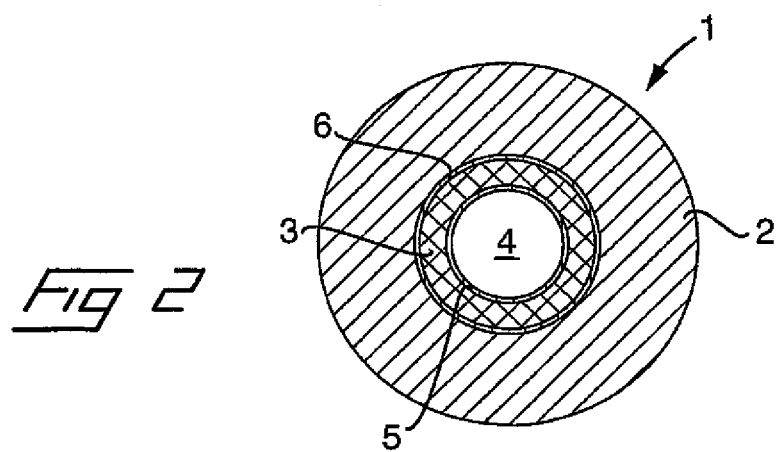
FIG. 2 is an end view of the piezoelectric sensor of FIG. 1.

With reference to FIGS. 1 and 2, a first embodiment of a piezoelectric sensor 1 is illustrated in a longitudinal section and in an end view, respectively. The sensor comprises a supporting substrate 2, which is tubular having a circular cross section. On the inner circumference, the supporting substrate 2 is covered with a piezoelectric layer 3 of a piezoelectric material. Accordingly, the piezoelectric sensor is formed as a tube having a cavity 4 in form of a through bore. To allow the piezoelectric material to serve as a sensor for purpose of measurement, the piezoelectric material is composed of aligned, polarized dipoles in a conventional fashion, well known in the art. In the illustrated embodiment, the supporting substrate is electrically insulating, being formed of for example ceramics or plastics. To detect the electrical signals generated in the piezoelectric layer when exposed to pressure, the piezoelectric layer is provided with an electrode layer 5, 6 on each side. More precisely one electrode layer 5 is applied to the inner circumference of the piezoelectric layer 3, whereas the other electrode layer 6 is applied between the piezoelectric layer and the supporting substrate 2. Each electrode layer 5, 6 is connected to an electric wire 7, 8, respectively, for transferring the generated electrical signals to a measuring or monitoring apparatus or the like. A piezoelectric sensor according to the embodiment illustrated in FIGS. 1 and 2, provides an open structure having a through bore 4 through which wires, coils, stylets or the like may pass when, for example, the piezoelectric sensor is positioned in a lead. To shield the piezoelectric layer from influence from ambient fluids, this sensor has to be built into a sealed in the structure of an object, e.g. a lead.

Figure 3:
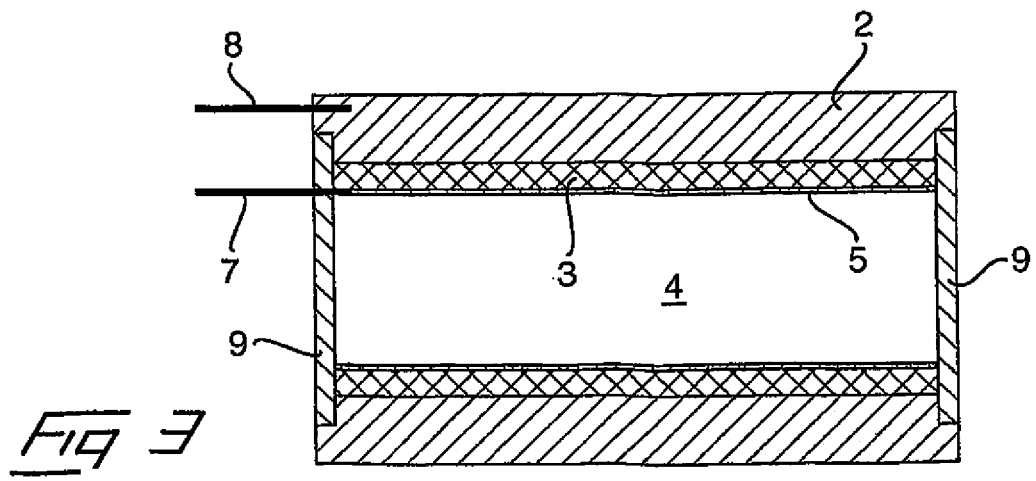
FIG. 3 is a longitudinal section through a piezoelectric sensor according to a second embodiment of the invention.

In FIG. 3 is shown a first alternative embodiment of a piezoelectric sensor according to the invention. In this embodiment the inner cavity 4 of the piezoelectric sensor, is sealed off from the environment by means of an electrically insulating end closure 9 at each end. In this way the requirement to build in the sensor fluid tight into an object, such as a lead, is not necessary any longer. Furthermore, the supporting substrate 2 is in this case formed of an electrically conducting material and, accordingly, serves as the outer electrode for the sensor and the connection wire 8 is connected to the supporting substrate. The connection wire 7 to the inner electrode layer 5, on the other hand, is passed through a through-connection in the end closure 9. One advantage with this embodiment is that the sensor can be made fluid tight already when manufactured, which has the result that the sensor need not be fluid tight built into an object. One disadvantage with this embodiment is, however, that the closed cavity excludes, or at least makes it more difficult, to let wires, coils, stylets and the like, pass through the inner cavity of the sensor.

Figure 4:
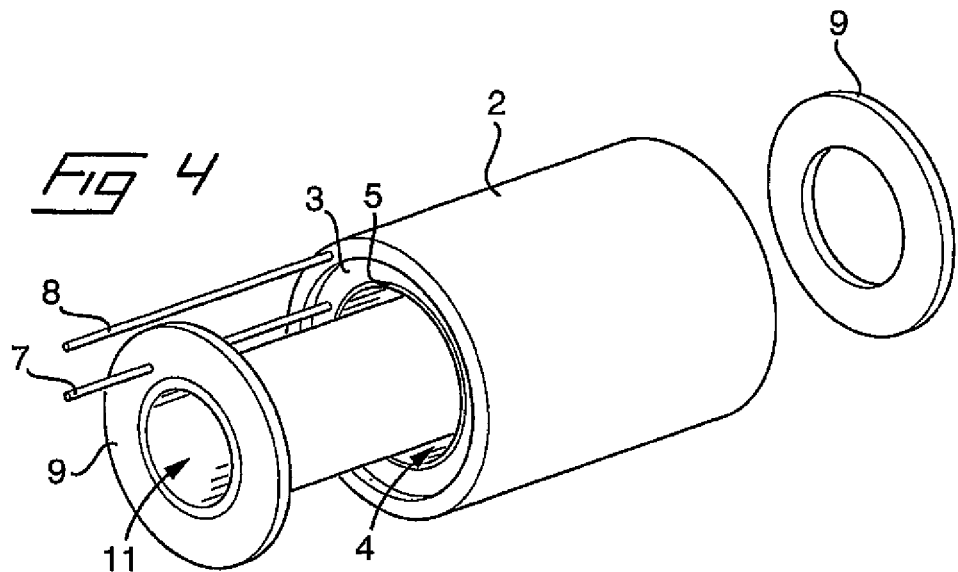
FIG. 4 is an exploded, perspective view of a piezoelectric sensor according to a third embodiment of the invention.
Figure 5:
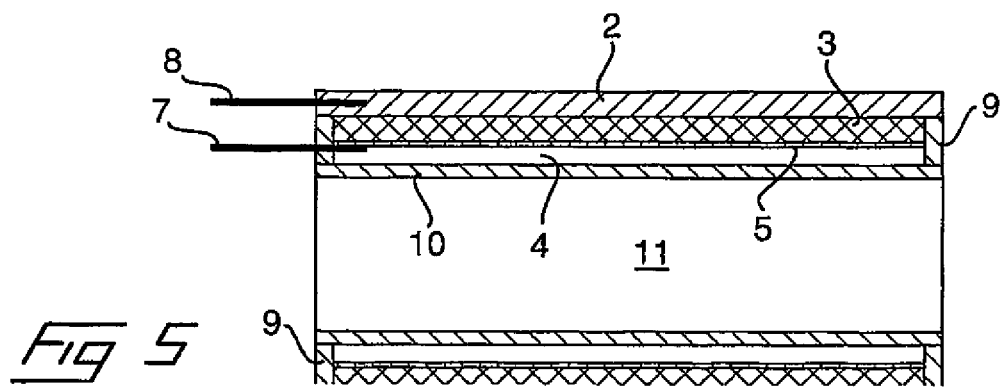
FIG. 5 is a longitudinal section through the piezoelectric sensor of FIG. 4.

This disadvantage is removed in a third alternative embodiment, as illustrated in FIGS. 4 and 5 in an exploded perspective view and a longitudinal section, respectively. Here an inner tube 10 is passed through each of the electrically insulating end closures 9, such that an annular, fluid tight cavity 4 is formed closest to the piezoelectric layer 3 and a through bore 11 is defined in the centre of the sensor. In all other respects the embodiment of FIGS. 4 and 5 is identical to the embodiment in FIG. 3. Consequently, the supporting substrate 2 is electrically conductive such that no electrode is required between the piezoelectric layer 3 and the supporting substrate 2.

Figure 6:
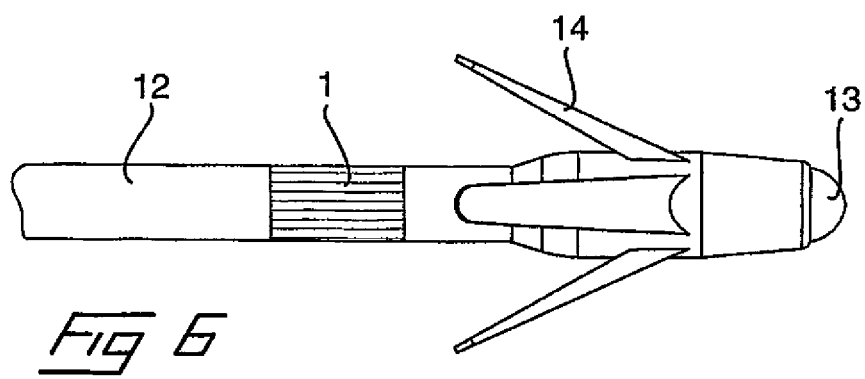
FIG. 6 is a side view of the distal end of an exemplary pacemaker lead embodying a piezoelectric sensor according to the present invention.

In FIG. 6 is illustrated a conceivable application and positioning of a piezoelectric sensor 1 according to the invention. Here is depicted a distal end of a pacemaker lead 12 which in the outermost end is provided with a point electrode 13, and a number of flexible times 14. The point electrode is adapted to be attached to tissue inside a human or animal body by being penetrated into the tissue, wherein the backwards pointing flexible times 14 will prevent the point electrode to slip out from the tissue again. The piezoelectric sensor 1 can in the illustrated position, be used to monitor the blood pressure and heart rate. If the outer supporting substrate of the sensor is an electrode, it can moreover be used as the second electrode in a bipolar pacemaker application for monitoring and pacing the rhythm of the heart.

Although modifications and changes may be suggested by those skilled in the art, it is the intention of the inventors to embody within the patent warranted heron all changes and modifications as reasonably and properly come within the scope of their contribution to the art.

We claim as our invention:

1. A piezoelectric sensor comprising a layer of a piezoelectric material having aligned, polarized dipoles, applied to a tubular supporting substrate, and having at least one electrode connected to an outer surface as well as at least one electrode connected to an inner surface, said piezoelectric material being applied on an inner circumference of the tubular supporting substrate;

an inner tube passed through a center of the sensor, and a pair of end closures connected to respective ends of the sensor, wherein the inner tube and end closures cooperate to define a fluid-tight cavity between the piezoelectric material and the inner tube.

2. A piezoelectric sensor according to claim 1, wherein the tubular supporting substrate serves as the outer electrode.

3. A piezoelectric sensor according to claim 1, wherein the tubular supporting substrate is formed with an inner cavity that is sealed off from the environment.

4. A piezoelectric sensor according to claim 3, wherein the tubular supporting substrate, in addition to the sealed off inner cavity, is formed with a through passage.

5. An implantable medical lead, comprising:

an elongate lead body configured for implantation in a subject;

a piezoelectric sensor carried by said elongate lead body, said piezoelectric sensor comprising a layer of a piezoelectric material having aligned, polarized dipoles, applied to a tubular supporting substrate, and having at least one electrode connected to an outer surface as well as at least one electrode connected to an inner surface of the layer, said piezoelectric material being applied on an inner circumference of the tubular supporting substrate; and an inner tube passed through a center of the sensor, and a pair of end closures connected to respective ends of the sensor, wherein the inner tube and end closures cooperate to define a fluid-tight cavity between the piezoelectric material and the inner tube.

* * * * *